(12) United States Patent
Tanaka et al.

(10) Patent No.: US 7,630,068 B2
(45) Date of Patent: Dec. 8, 2009

(54) METHOD AND SYSTEM OF DEFECT INSPECTION FOR MASK BLANK AND METHOD OF MANUFACTURING SEMICONDUCTOR DEVICE USING THE SAME

(75) Inventors: Toshihiko Tanaka, Tokyo (JP); Tsuneo Terasawa, Tokyo (JP); Yoshihiro Tezuka, Tsukuba (JP)

(73) Assignee: Renesas Technology Corporation, Tokyo (JP)

( * ) Notice: Subject to any disclaimer, the term of this patent is extended or adjusted under 35 U.S.C. 154(b) by 334 days.

(21) Appl. No.: 11/707,127

(22) Filed: Feb. 16, 2007

(65) Prior Publication Data

US 2007/0188743 A1    Aug. 16, 2007

(30) Foreign Application Priority Data

Feb. 16, 2006    (JP)    ............... 2006-039253

(51) Int. Cl.
*G01N 21/88* (2006.01)
*G01N 21/00* (2006.01)

(52) U.S. Cl. ............... 356/237.1; 356/237.4; 250/492.2; 250/372

(58) Field of Classification Search ... 356/237.1–237.6; 250/492.1, 492.2, 559.22, 237; 382/240; 359/858, 859, 366; 378/34, 43, 70
See application file for complete search history.

(56) References Cited

U.S. PATENT DOCUMENTS

| | | | | |
|---|---|---|---|---|
| 4,749,840 A | * | 6/1988 | Piwczyk | 219/121.68 |
| 5,131,023 A | * | 7/1992 | Yasugaki et al. | 378/43 |
| 5,151,609 A | * | 9/1992 | Nakagawa et al. | 250/559.22 |
| 5,177,774 A | * | 1/1993 | Suckewer et al. | 378/43 |
| 5,331,456 A | * | 7/1994 | Horikawa | 359/350 |
| 5,619,382 A | * | 4/1997 | Kato et al. | 359/858 |
| 5,808,312 A | * | 9/1998 | Fukuda | 250/492.2 |
| 6,042,995 A | * | 3/2000 | White | 430/311 |
| 6,522,717 B1 | * | 2/2003 | Murakami et al. | 378/43 |
| 6,555,828 B1 | * | 4/2003 | Bokor et al. | 250/492.2 |
| 6,617,603 B2 | | 9/2003 | Ishiguro et al. | |
| 6,738,135 B1 | * | 5/2004 | Underwood et al. | 356/237.5 |
| 6,954,266 B2 | | 10/2005 | Tomie | |

(Continued)

FOREIGN PATENT DOCUMENTS

JP    7-287389    4/1994

(Continued)

*Primary Examiner*—Sang Nguyen
(74) *Attorney, Agent, or Firm*—Stites & Harbison PLLC; Juan Carlos A. Marquez, Esq.

(57) ABSTRACT

Defect detection is performed with two settings, that is, setting of a focus position where a signal intensity obtained from a dot pattern is maximum and setting of a focus position where a signal intensity obtained from a hole pattern is maximum. In addition, defect detection is performed at a predetermined focus position previously set and for the detected defect, the focus position is changed at that position to find a focus position where the signal intensity is maximum. If the focus position is away from a signal light-receiving system, the defect is determined as dot-shaped. If the focus position is close to the signal light-receiving system, the defect is determined as hole-shaped. If the focus position is intermediate of them, the defect is determined as an elongated-shaped.

2 Claims, 6 Drawing Sheets

U.S. PATENT DOCUMENTS

| | | | |
|---|---|---|---|
| 7,005,649 B1 * | 2/2006 | Tezuka et al. | 250/372 |
| 7,282,305 B2 | 10/2007 | Shoki et al. | |
| 2004/0057107 A1 | 3/2004 | Yun et al. | |
| 2005/0196059 A1 * | 9/2005 | Inoue et al. | 382/240 |

FOREIGN PATENT DOCUMENTS

| | | |
|---|---|---|
| JP | 2001-174415 | 12/1999 |
| JP | 2003-114200 | 10/2001 |
| JP | 2005-66781 | 8/2003 |
| JP | 2004-289110 | 9/2003 |

* cited by examiner

METHOD AND SYSTEM OF DEFECT INSPECTION FOR MASK BLANK AND METHOD OF MANUFACTURING SEMICONDUCTOR DEVICE USING THE SAME

CROSS-REFERENCE TO RELATED APPLICATION

The present application claims priority from Japanese Patent Application No. JP 2006-39253 filed on Feb. 16, 2006, the content of which is hereby incorporated by reference into this application.

TECHNICAL FIELD OF THE INVENTION

The present invention relates to a method and system of defect inspection for mask blanks, and a method of manufacturing semiconductor device using such method and system for EUVL (Extreme Ultraviolet Lithography) using extreme short-wavelength light. More particularly, to a technology effectively applied to defect inspection, adaptive to a fine pattern, on a multilayer mask blank with high defect detection sensitivity.

BACKGROUND OF THE INVENTION

About mask blank defect inspection, examples of technologies studied by the inventors are as follows.

Semiconductor devices are mass-produced by repeatedly using an optical lithography process in which a mask, which is an original plate with a circuit pattern drawn thereon, is irradiated with exposure light and the pattern is then transferred onto a semiconductor substrate (hereinafter, referred to as a "wafer") via a reduction optics.

In recent years, microfabrication of semiconductor devices has progressed, and a method of further decreasing the exposure wavelength of optical lithography to increase a resolution has been studied. Although ArF lithography using argon-fluoride (ArF) excimer laser light having a wavelength of 193 nm has been developed until now, development of EUVL (Extreme Ultraviolet Lithography) having an extremely short wavelength of 13 nm has proceed. For this wavelength band, transmissive masks cannot be used due to optical absorption by the multilayered film. Therefore, a multilayered-film (i.e., multilayer) reflective mask using reflection (Bragg reflection) by a multilayer made of, for example, molybdenum (Mo) and silicon (Si), is used as a mask for EUVL. Multilayer reflection uses a type of interference. In EUVL, a reflective mask is used with an absorber pattern being formed on a multilayer blank with a multilayer film made of, for example, Mo and Si, adhering to a quartz glass or low-thermal-expansion glass substrate.

On the other hand, until ArF lithography, a transparent mask having an absorber made of, for example, chromium (Cr) formed on a glass substrate made of, for example, quartz, which is transparent for the exposure wavelength has been used.

In EUVL, due to the facts that the reflective mask using Bragg reflection and the extremely short exposure wavelength of 13 nm, even if there occurs an extremely slight abnormality in height with a fraction of the exposure wavelength, a local difference in reflectivity occurs at that abnormal part. It causes a defect at the time of printing. Compared with the conventional transmissive mask, there is a different in quality regarding defect printing.

Examples of a scheme for mask blank defect inspection include a scheme of radiating a mask blank with laser light from an oblique direction to detect a foreign substance from its diffused light and a technology of detecting defects by using light having the same wavelength as the wavelength for use in exposure, which is called an "at-wavelength" defect inspection technique. Examples of the latter scheme include a scheme of using a darkfield image (for example, refer to Japanese Patent Application Laid-Open Publication No. 2003-114200, which is referred to as Patent Document 1 hereinafter), an X-ray microscope scheme using the brightfield, and a combined scheme of using the darkfield to detect defects and using a Fresnel zone plate in the brightfield system to identify the defects (for example, refer to United States Patent Application Publication No. 2004/0057107, which is referred to as Patent Document 2).

Examples of a conventional scheme for inspecting a transmissive mask blank include a scheme of radiating the mask blank with laser light from an oblique direction to detect a foreign substance from its diffused light and a scheme of detecting a brightfield image (microscope image). Modifications of the latter scheme include a scheme of determining a convex defect or a concave defect based on the asymmetry of the detection image signal (for example, refer to Japanese Patent Application Laid-Open Publication No. 2001-174415, which is referred to as Patent Document 3 and Japanese Patent Application Laid-Open Publication No. 2002-333313, which is referred to as Patent Document 4).

SUMMARY OF THE INVENTION

Here, as a result of studies by the inventors, the following has been revealed regarding the above-described mask blank defect inspection technology.

For example, the conventional scheme has any of the following problems: (a) Due to low defect detection sensitivity, a defect that will become a printing defect is overlooked; (b) Due to a long inspection time, the scheme cannot be practically used with its throughput; and (c) The apparatus is complex and high cost. Such problems can be reorganized by respective schemes as follows.

(1) In the schemes using laser light, such as Patent Document 3 and Patent Document 4, detection sensitivity is insufficient. This includes a problem of resolution and a problem of phase detection, which relate to a matter of physical nature. That is, the problem of resolution occurs because, although an extremely fine pattern printing which is finer than 50 nm is required in EUVL, light having a wavelength which is several times longer than the required wavelength is used. Moreover, since a multilayer mask blank is used for the EUVL mask, detection sensitivity for detecting phase defects is extremely low with the inspection light having a wavelength different from that of the exposure light.

(2) In the conventional technology of inspection on a certain focus plane such as the schemes disclosed in Patent Document 1 and Patent Document 2, the scheme of detection by exposure wavelength using darkfield images has a problem in which sufficient inspection sensitivity cannot always be achieved and a problem in which it is impossible to determine the defect type, that is, whether the defect is a convex defect or a concave defect.

(3) In the scheme of microscope detection by exposure wavelength using brightfield, resolution is excellent and the defect type can be identified. However, since the pixel size in a detection-light-receiving system has to be small, the amount of data is enormous, causing a problem in which the inspection throughput is several orders of magnitude slower than that at a required practical level.

(4) The brightfield and darkfield combined scheme for detection by exposure wavelength, such as the scheme disclosed in Patent Document 2, has a problem in which the apparatus is complex and a problem in which detection sensitivity in the high-speed darkfield scheme is low.

Therefore, an object of the present invention is to provide a technology allowing high defect detection sensitivity and high-speed inspection in mask blank defect inspection.

In addition, another object of the present invention is to provide a technology capable of determining the type of defect in mask blank defect inspection.

The above and other objects and novel characteristics of the present invention will be apparent from the description of this specification and the accompanying drawings.

The typical ones of the inventions disclosed in this application will be briefly described as follows.

The mask blank defect inspection method and defect inspection system according to the present invention performs mask blank defect detection by setting a focus position (focus level) where the signal intensity of a darkfield detection image of a dot-shaped pattern is maximum and/or a focus position where the signal intensity of a darkfield detection image of a hole-shaped pattern is maximum.

In addition, in the method and system of mask blank defect inspection according to the present invention, defect detection is performed at a predetermined focus position (focus level) previously set and, for the detected defect, the focus position is changed at that position to find a focus position where the signal intensity is maximum. If the focus position is away from a signal light-receiving system, the defect is determined as being hole-shaped. If the focus position is closer to the signal light-receiving system, the defect is determined as being dot-shaped. If the focus position is in a direction intermediate, the defect is determined as being a line (elongated)-shaped.

Furthermore, the method of manufacturing semiconductor device according to the present invention is to manufacture semiconductor devices by using a mask blank inspected by using the method of mask blank defect inspection described above.

The effects obtained by typical aspects of the present invention will be briefly described below.

(1) Defect inspection sensitivity is improved, thereby enabling detection of even small defects.

(2) It is possible to identify whether the defect is hole-shaped, dot (swell)-shaped, or so-called line-shaped, which is elongated in one direction. This is useful in selecting a defect correcting method and developing a defect reduction process.

(3) Such improvement in defect inspection sensitivity and ability of defect-type determination contribute to improvement in influences on transfer and mask blank quality. Accordingly, yields of semiconductor devices improve.

BRIEF DESCRIPTIONS OF THE DRAWINGS

DESCRIPTIONS OF THE PREFERRED EMBODIMENTS

Hereinafter, embodiments of the present invention will be described in detail with reference to the accompanying drawings. Note that components having the same function are denoted by the same reference symbols throughout the drawings for describing the embodiment, and the repetitive description thereof will be omitted.

First Embodiment

Figure 1:
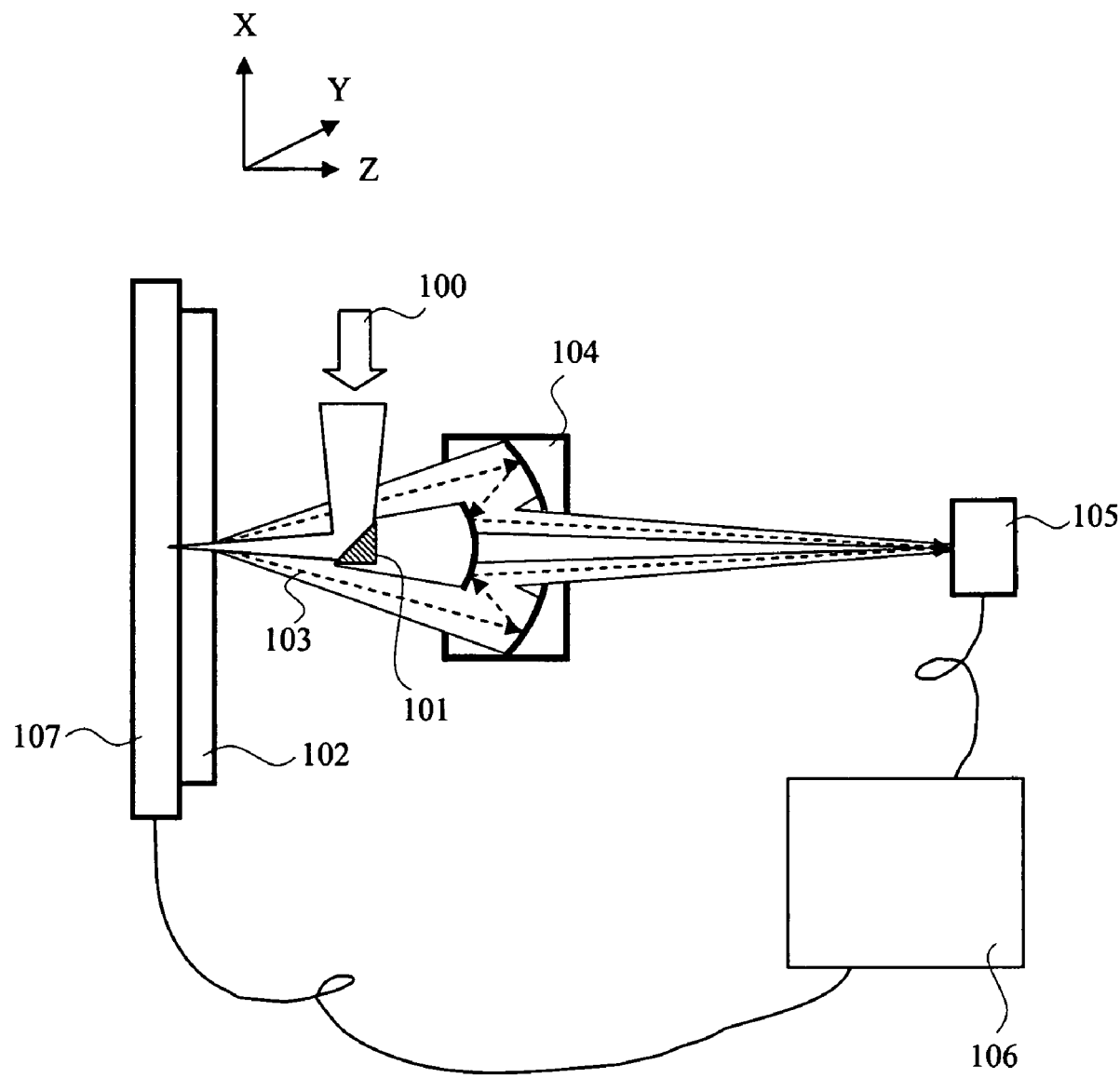
FIG. 1 is a schematic diagram of a configuration and operation of a mask blank defect inspection system according to a first embodiment of the present invention.
Figure 2A:
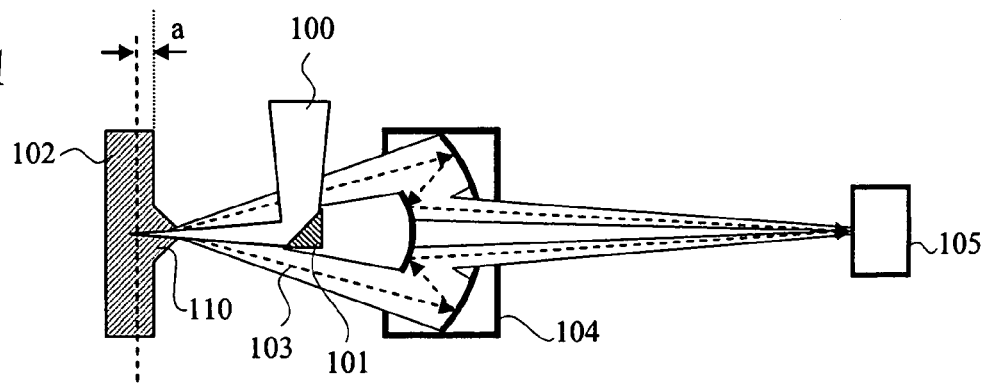
FIG. 2A is a diagram for describing a concept of a defect inspection method in the mask blank defect inspection system according to the first embodiment of the present invention.
Figure 2B:
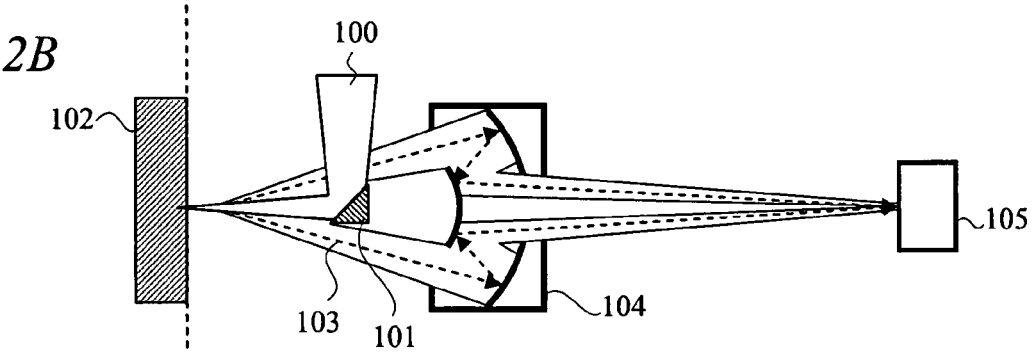
FIG. 2B is a diagram for describing the concept of the defect inspection method in the mask blank defect inspection system according to the first embodiment of the present invention.
Figure 2C:
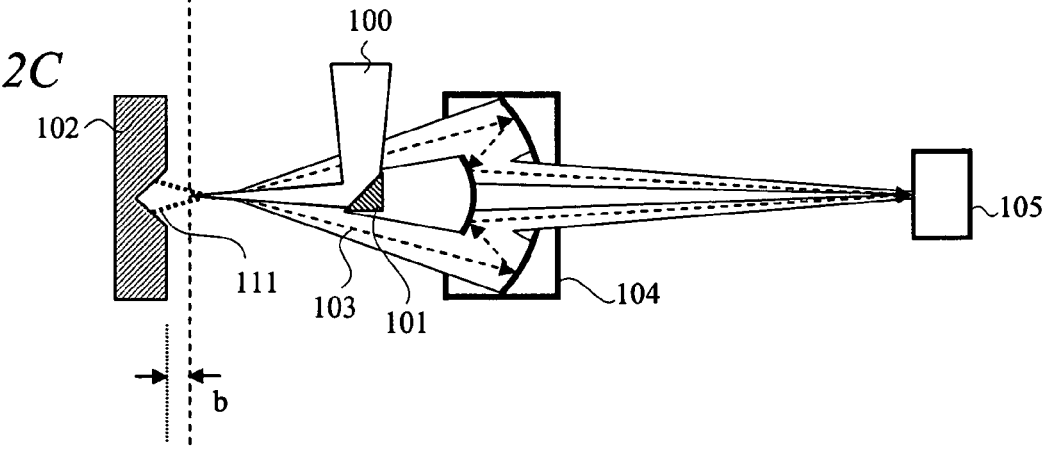
FIG. 2C is a diagram for describing the concept of the defect inspection method in the mask blank defect inspection system according to the first embodiment of the present invention.
Figure 3:
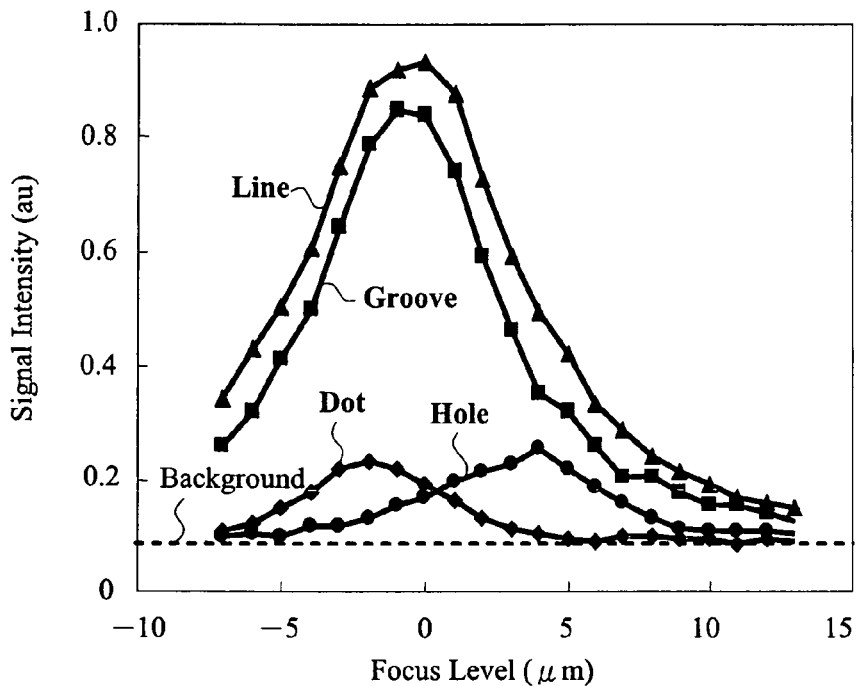
FIG. 3 is a characteristic diagram depicting characteristics of defect signals in the mask blank defect inspection system according to the first embodiment of the present invention.
Figure 4:
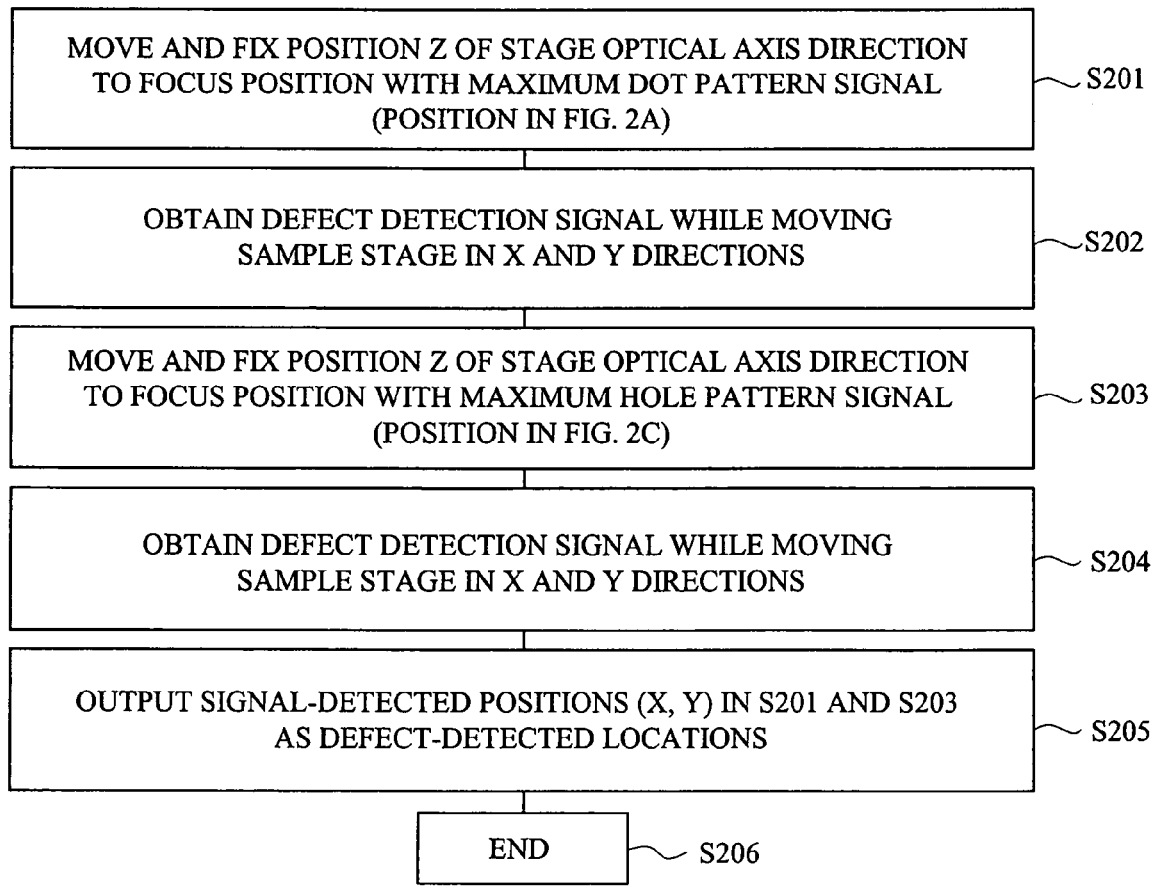
FIG. 4 is a process flow diagram of an implementing process of a defect inspection method in the mask blank defect inspection system and method according to the first embodiment of the present invention.

FIG. 1 is a schematic diagram of a configuration and operation of a system for mask blank defect inspection according to a first embodiment of the present invention. FIGS. 2A, 2B, 2C are diagrams for describing a concept of a defect inspection method in the mask blank defect inspection system according to the first embodiment of the present invention. FIG. 3 is a characteristic diagram depicting characteristics of defect signals. FIG. 4 is a process flow diagram of an implementing process of a defect inspection method. First, with reference to FIG. 1, one example of the configuration of the mask blank defect inspection system according to the first embodiment is described. The mask blank defect inspection system according to the first embodiment comprises: for example, a darkfield optical system and imaging system including a mask stage 107 movable in X-axis, Y-axis, and Z-axis directions, a mirror 101 that is introduced extreme ultraviolet light 100 (hereinafter, referred to as "EUV light") to radiate it onto a mask blank (sample) 102 on the mask stage 107, an image detector 105, and a magnifying/imaging lens 104 that catches scatter-reflected light 103 from the mask blank 102 to form an image on the image detector 105; and a signal analyzing device 106 that analyzes a signal from such a system.

In the first embodiment, since the radiated light is an EUV light, the magnifying/imaging lens 104 is a catoptric system, and a Schwarzschild optical system is used herein. Although the magnification is 20×, this is merely a experimental condition and is therefore not restrictive. The magnification may be, for example, 26×.

As the image detector 105, a TDI (Time Delay Integration) sensor is used. The pixel size is sufficiently large compared with wavelength resolution. In the first embodiment, the size of the sensor per pixel is 13 μm×13 μm. Here, the image detector 105 is not restricted to such a TDI sensor, and another sensor may be used.

The mask blank 102 can be freely moved in an X-axis direction (in FIG. 1, a vertical direction on the sheet) and a Y-axis direction (in FIG. 1, a perpendicular direction on the sheet) by scanning-movement (successive movement) of the mask stage 107. In addition, the mask stage 107 has a mechanism of moving also in a Z-axis direction along a lens optical axis (in FIG. 1, a horizontal direction on the sheet), that is, a direction toward/backward the magnifying/imaging lens 104. X, Y, and Z positions of the mask stage 107 are monitored, and its positional information is transmitted to the signal-analyzing device 106.

Next, with reference to FIGS. 2A, 2B, 2C, FIG. 3, and FIG. 4, the operation of the mask blank defect inspection system according to the first embodiment is described.

First, as shown in FIGS. 2A and 2C, the multilayer mask blank for setting 102 (first and third mask blanks) having formed thereon a dot-shaped pattern 110 and a hole-shaped pattern 111, respectively serving as a reference is radiated with EUV light. Then, the mask stage 107 is moved in the Z-axis direction to find a focus position (first and second focus positions) where its intensity is maximum. The height of the dot-shaped pattern 110 and the depth of the hole-shaped pattern 111 are as small as on the order of 6 nm.

Compared with a focus position from a so-called line-shaped pattern having an elongated shape as shown in FIG. 2B, where the signal intensity is maximum, the focus position in FIGS. 2A and 2C is shifted by the distance denoted with "a" and "b", respectively, in the case of dot and hole. In view of image formation in a brightfield, when an upper surface of the hole-shaped pattern (convex pattern) is focused, the focus position is supposed to be shifted in a direction opposite to that shown in FIG. 2A and when an upper surface of the hole-shaped pattern (concave pattern) is focused, the focus position is supposed to be shifted in a direction opposite to that shown in FIG. 2C. However, the signal intensity was maximum in the directions shown in FIGS. 2A and 2C, opposite to those supposed to be.

Here, the dot-shaped pattern means a pattern having a swelled shape in a cone, frustum, pyramid, or prismoid shape. The hole-shaped pattern means a pattern having a recessed shape in a cone, frustum, pyramid, or prismoid shape.

In FIG. 2B, although the mask blank 102 is drawn as a flat shape, this is to distinguish the mask blank 102 from the dot and hole, and the mask blank 102 actually has a pattern of elongated lines. With the focus position where the signal intensity is maximum serving as the reference position, the focus positions where the signal intensity of the dot-shaped pattern and the hole-shaped pattern is maximum are shown.

FIG. 3 shows a focus position (level) dependency of the signal intensity with respect to various patterns. In FIG. 3, the horizontal axis represents the focus position (focus level), whilst the vertical axis represents the signal intensity of darkfield detection image. As the value of the focus position is larger, the position of the mask stage 107 is away from the magnifying/imaging lens 104 and the image detector 105. "Dot" represents the dot-shaped pattern 110, whilst "Hole" represents the hole-shaped pattern 111. "Groove" represents a line-shaped concave pattern, whilst "Line" represents a line-shaped convex pattern. The pattern is regarded as line-shaped if the ratio between the line width and the line length is greater than two. Between line-shaped patterns (in comparison between Groove and Line), a difference in focus position is slight enough to be within a depth of focus (approximately 2 μm). By contrast, a difference in focus position where the signal intensity is maximum between Dot and Hole, which are two-dimensional shapes, is significantly varied, exceeding the depth of focus largely. Here, experiments were performed on patterns having dimensions of 90 nm to 1000 nm.

Next, the mask blank 102 (second mask blank), which is an inspection target, is set on the mask stage 107. Then, as shown in FIG. 4, the focus position is fixed to the position (first focus position) for the dot-shaped pattern 110 of FIG. 2A (step S201). The mask stage 107 is then does the scanning-movement in X-axis and Y-axis directions for horizontal movement, thereby obtaining a darkfield detection signal (step S202).

Next, the focus position is fixed to the position (second focus position) for the hole-shaped pattern 111 of FIG. 2C (step S203). The mask stage 107 is then does the scanning-movement in X-axis and Y-axis directions, thereby obtaining a darkfield detection signal (step S204). Then, the position where the signal is obtained is determined as a position with a defect and is outputted (step S205). The defect inspection procedure is then terminated (step S206).

In addition, optionally, if the signal intensity of the focus position in FIG. 2C is stronger than that in FIG. 2A and if a signal is observed only at the focus position in FIG. 2C, it is determined that a hole-shaped defect is present.

Here, for an elongated defect such as a line or groove, although the focus position where the maximum signal is obtained is slightly different from that of a dot-shaped pattern, such an elongated pattern has a large total pattern area from which a signal intensity easily obtained, and therefore there was no problem when signal obtainment at that focus position was omitted. Here, there was no problem when the order of the signal obtaining process at the focus position with a maximum dot pattern signal (steps S201 and S202) and the signal obtaining process at the focus position with a maximum hole pattern signal (steps S203 and S204) was reversed.

Also, there is one scheme in which the mask stage 107 is semi-fixed in the Z-direction for scanning movement in the X and Y directions, image data is subsequently transferred to the signal analyzing system, and then the mask stage 107 is moved in the Z-direction with scanning movement again in the X and Y directions. Also there is another scheme in which the mask stage 107 is moved in the Z-direction at certain X and Y positions while its movement in the X and Y directions is step-wise. However, since enormous amount of image data should be obtained, unmoving time for transferring picked-up image data is long. Therefore, the scanning movement scheme was superior in throughput to the latter scheme.

As a result of defect detection with the focus position being fixed through the above-described scheme, detection sensitivity was improved compared to the conventional scheme. In the conventional scheme, a hole defect having a diameter of 130 nm was overlooked. In the first embodiment, however, with the present scheme, even a hole defect having a diameter of 90 nm was able to be detected as well as a dot defect of 70 nm.

Here, a setting tolerance and a depth of focus of the focus for obtaining the maximum signal were approximately ±1 µm.

Second Embodiment

Figure 5:
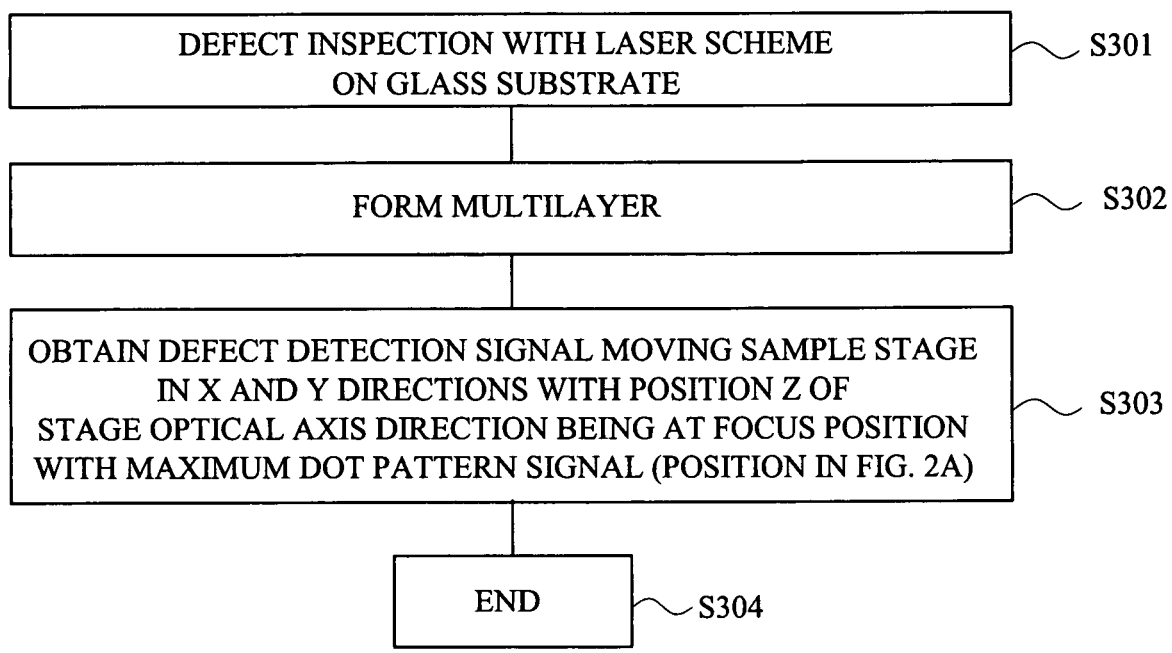
FIG. 5 is a process flow diagram of an implementing process of a defect inspection method in a mask blank defect inspection system and method according to a second embodiment of the present invention.

FIG. 5 is a process flow diagram of an implementing process of a defect inspection method in a system and method for mask blank defect inspection according to a second embodiment of the present invention.

Most hole-shaped defects, in other words, pit-shaped defects, are mainly formed in a step for glass substrate before forming multilayer.

Therefore, in the second embodiment, defect inspection is first performed by using a laser light in the step for glass substrate (step S301).

Then, a multilayer is formed on the glass substrate to form a mask blank 102 (second mask blank), which is an inspection target (step S302).

After that, with the mask blank 102 being fixed to a focus position where the signal intensity is maximum for a dot-shaped defect (position in FIG. 2A: first focus position), a darkfield defect detection using an EUV light is performed (step S303). Then, a signal-detected position is outputted and then terminate the inspection (step S304). With this scheme, defect screening can be performed at an early step for the glass-substrate. In addition, the time for defect inspection using EUV light can be reduced.

Third Embodiment

Figure 6:
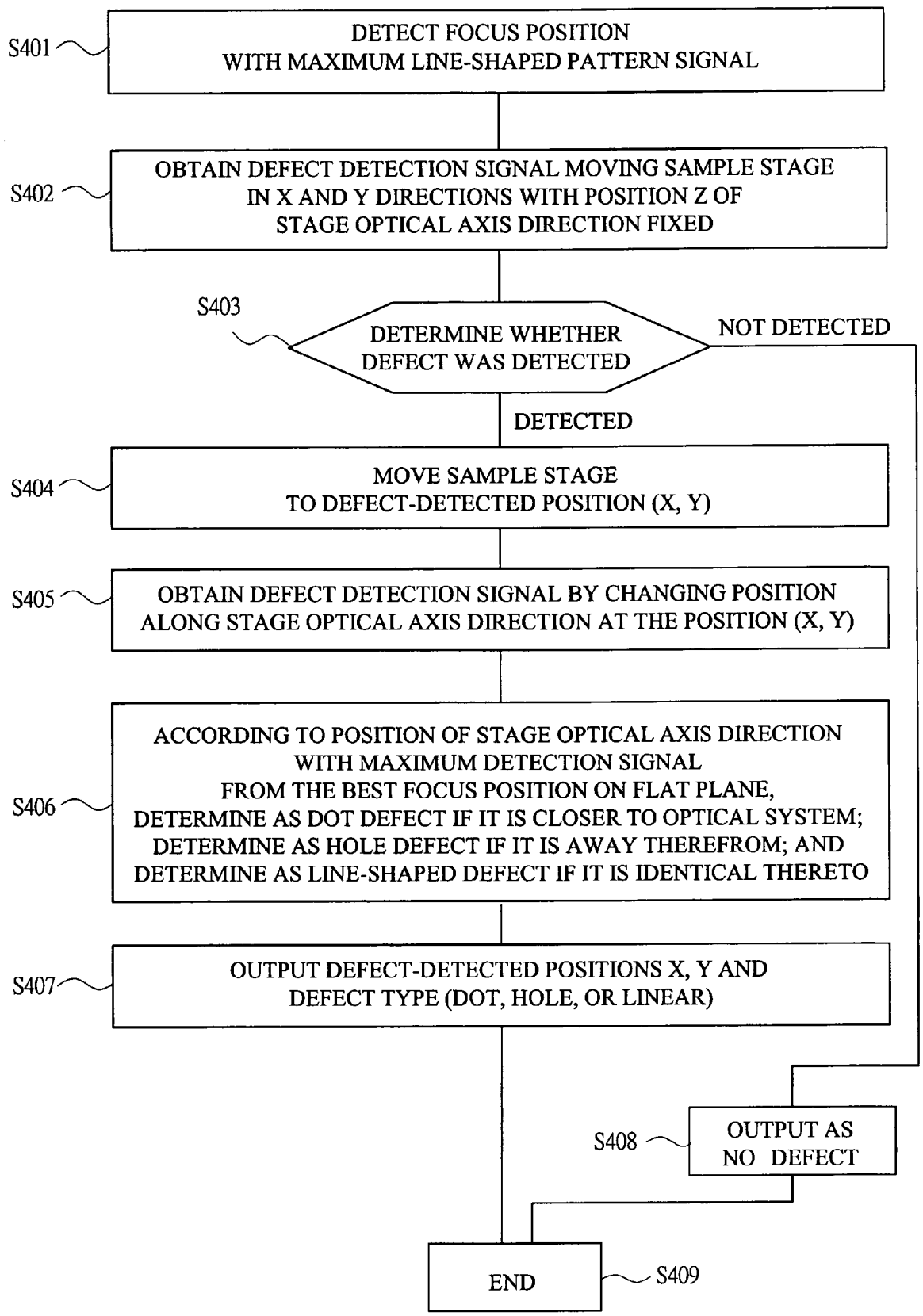
FIG. 6 is a process flow diagram of an implementing process of a defect inspection method in a mask blank defect inspection system and method according to a third embodiment of the present invention.

FIG. 6 is a process flow diagram of an implementing process of a defect inspection method in a system and method for mask blank defect inspection according to a third embodiment of the present invention.

In the third embodiment, the defect type of the mask blank is determined.

First, a best focus position (third focus position) on a flat plane is found in advance (step S401). The best focus position is assumed to be a focus position with a maximum line-shape pattern signal, which is found by using a reference mask blank (fourth mask blank). This mask blank is a multilayer mask blank with the thickness of the substrate accurately known. On that multilayer mask blank, a line-shaped pattern serving as a reference for setting the focus position is formed. As such a line-shaped pattern, a convex-line-shaped or groove-shaped pattern is formed.

This focus position finding step is not necessarily performed for each implemented sample mask blank (second mask blank), and may be performed at the first time and at the time of quality control (QC) in apparatus management. In addition, if the presence of a position-specified line-shaped defect on the implemented sample mask blank is known in advance, this defect can be used for this focus position detection. To increase accuracy in focus position detection, the line-shaped pattern is preferably narrow in line width and low in height, such as 2 nm.

Then, with the height of the mask stage 107 fixed to the best focus position (third focus position), the mask stage 107 is moved in the X and Y directions to monitor a darkfield image for signal detection (step S402).

Then, a position where the signal intensity exceeds a background signal level is determined as a defect (step S403). When a defect is not detected, an output is produced as no defect (step S408). When a defect is detected, the mask stage 107 is moved to the position where the defect was detected (step S404). At that position, the position of the stage optical-axis direction (Z direction) is changed to obtain a defect detection signal in a darkfield imaging system (step S405).

According to the position of stage optical-axis direction with maximum detection signal (fourth focus position) from the best focus position on the flat plane (third focus position), the defect is determined as: dot-shaped defect if the position is closer to the darkfield imaging lens system; hole-shaped if the position is away from the darkfield imaging lens system; and line-shaped if the position is identical to that of the flat plane (step 406). The shape determination result is outputted with the defect-detected position (step S407), and then the defect detection procedure is terminated (step S409).

Here, the amount of step-wise movement of the focus position is 2 µm. Then, the sample mask blank is unloaded, for example. With this scheme, it is possible to determine the presence or absence of a defect and its defect type (shape) in a non-destructive manner. Here, the time required for a series of measurement is four hours for the entire surface of the mask blank.

Fourth Embodiment

FIGS. 7A to 7F are sectional views of main parts that depict a semiconductor device manufacturing process according to a fourth embodiment of the present invention.

In the fourth embodiment, the first to third embodiments are applied to manufacturing of semiconductor devices having a CMIS (Complimentary MIS) circuit of twin-well type.

Figure 7A:
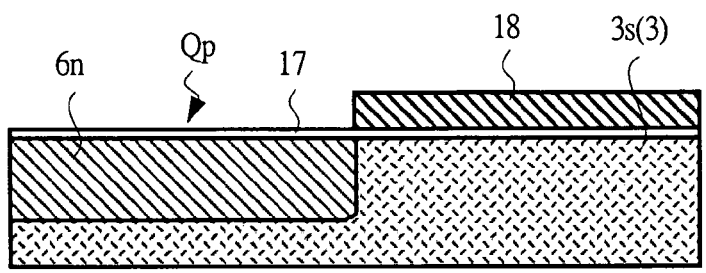
FIG. 7A is a sectional view of main parts that depicts a semiconductor device manufacturing process according to a fourth embodiment of the present invention.
Figure 7B:
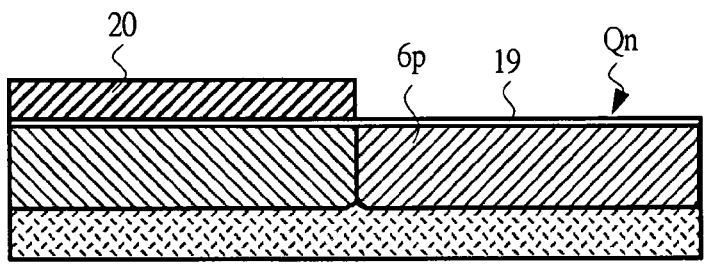
FIG. 7B is a sectional view of main parts that depicts the semiconductor device manufacturing process according to the fourth embodiment of the present invention.

With reference to FIGS. 7A to 7B, which are sectional views of main parts of a semiconductor wafer in the manufacturing process, the semiconductor device manufacturing process is described.

A semiconductor substrate 3s forming a semiconductor wafer 3 is formed of, for example, single crystal silicon (Si) having a circular n-type flat surface. On its top, for example, an n-well 6n and a p-well 6p are formed. The n-well 6n has introduced thereto an n-type impurity of phosphorus (P) or arsenic (As), for example. Also, the p-well 6p has introduced thereto a p-type impurity of boron (B), for example. These n-well and p-well are formed in a manner as follows.

First, a wafer alignment mark for mask alignment is formed on the semiconductor substrate 3s (not shown). This wafer alignment mark can be formed at the time of forming the well by adding a selective oxidization process.

Then, as shown in FIG. 7A, an oxide film 17 is formed on the semiconductor substrate 3s, and then a resist pattern 18 for implantation mask is formed on the oxide film 17 through lithography. Then, phosphorus is ion-implanted.

Then, ashing is performed to remove the resist pattern 18. After the oxide film 17 is removed, as shown in FIG. 7B, an oxide film 19 is formed on the semiconductor substrate 3s, and then a resist pattern 20 for implantation mask is formed on the oxide film 19 through lithography. Then, phosphorus is ion-implanted.

Figure 7C:
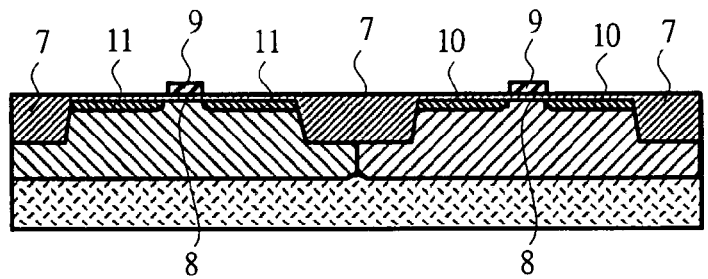
FIG. 7C is a sectional view of main parts that depicts the semiconductor device manufacturing process according to the fourth embodiment of the present invention.
Figure 7D:
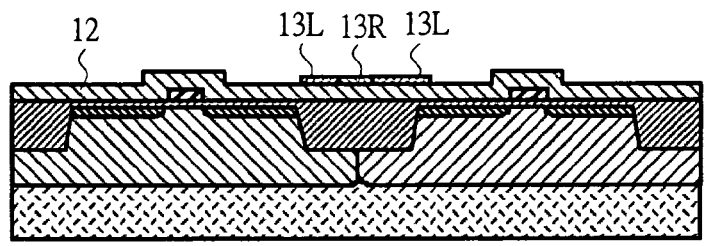
FIG. 7D is a sectional view of main parts that depicts the semiconductor device manufacturing process according to the fourth embodiment of the present invention.

Then, the resist pattern 20 and the oxide film 19 are removed. Then, a field insulating film 7 for isolation made of, for example, a silicon oxide film, is formed on a main surface (first main surface) of the semiconductor substrate 3s in a form of trench isolation (FIG. 7C). In active regions surrounded by this field insulating film 7, nMISQn and pMISQp are formed. A gate insulating film 8 of nMISQn and pMISQp is formed of, for example, a silicon oxide film. Also, a gate electrode 9 of nMISQn and pMISQp is formed through lithography after depositing a gate forming film made of, for example, low-resistant polysilicon through CVD or the like, and then through etching. Such lithography in this process is called gate lithography. For this gate lithography, extremely fine pattern transfer with high dimensional accuracy is required.

Semiconductor regions 10 of nMISQn are formed in a self-aligned manner onto the gate electrode 9 by introducing, for example, phosphorus or arsenic, to the semiconductor substrate 3s through ion implantation or the like with the gate electrode 9 as a mask. Also, semiconductor regions 11 of pMISQp are formed in a self-aligned manner onto the gate electrode 9 by introducing, for example, boron, to the semiconductor substrate 3s through ion implantation or the like with the gate electrode 9 as a mask.

However, the gate electrode 9 is not restricted to be formed of a simple-body film of, for example, low-resistant polysilicon, but can be variously changed. Alternatively, the gate electrode may have so-called a polysilicide structure with a silicide layer made of, for example, tungsten silicide or cobalt silicide, being provided on the low-resistant polysilicon film, for example. Still alternatively, the gate electrode may have so-called a polymetal structure with a metal film made of, for example, tungsten, through a barrier conductive film made of, for example, titanium nitride or tungsten nitride, being provided on the low-resistant polysilicon film, for example.

First, on the semiconductor substrate 3s described above, as shown in FIG. 7D, an interlayer dielectric 12 made of, for example, a silicon oxide film, is deposited through CVD or the like, and then a polysilicon film is deposited thereon through CVD or the like. Then, lithography is performed on that polysilicon film. Then, after etching and patterning, impurities are introduced to a predetermined region of the patterned polysilicon film, thereby forming a wiring 13L and a resistor 13R made of the polysilicon film.

Figure 7E:
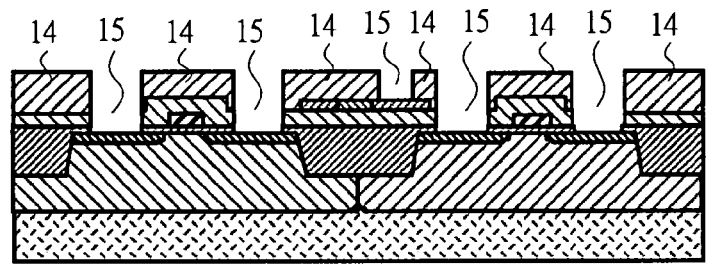
FIG. 7E is a sectional view of main parts that depicts the semiconductor device manufacturing process according to the fourth embodiment of the present invention.

After that, as shown in FIG. 7E, on the semiconductor substrate 3s, a silicon oxide film 14, for example, is deposited through CVD or the like. Then, connection holes 15 are formed on the interlayer dielectric 12 and the silicon oxide film 14 through lithography and etching so that part of the semiconductor regions 10 and 11 and the wiring 13L is exposed. Since fine holes are difficult to resolve due to influences of optical diffraction, a lithography technique with high resolution is applied to the lithography for the connection holes.

Figure 7F:
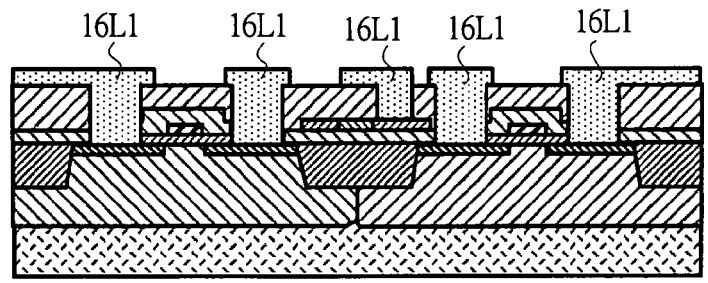
FIG. 7F is a sectional view of main parts that depicts the semiconductor device manufacturing process according to the fourth embodiment of the present invention.

Furthermore, on the semiconductor substrate 3s, metal films made of titanium (Ti), titanium nitride (TiN), and tungsten (W) are sequentially deposited through spattering and CVD. Then, these metal films are subjected to lithography and etching, thereby forming a first-layer wiring 16L1 as shown in FIG. 7F. The first-layer wiring includes a fine dense pattern and an isolated pattern, and has a complex layout shape because of wire routing and wire connection by avoiding adjacent wires. For this reason, lithography for the first-layer wiring requires high resolution and dimensional accuracy. Thereafter, a second-layer wiring and the subsequent are formed in a manner similar to that of the first-layer wiring 16L1, thereby manufacturing a semiconductor device.

In this series of the semiconductor device manufacturing processes, as lithography for the gate layer, connection holes, and the first-layer wiring, an EUVL lithography is used. Furthermore, as masks for the gate layer and the first-layer wiring, those subjected to mask blank inspection through the apparatus and method according to the first to third embodiments are used, which are confirmed as having no defect in the mask blank state.

Furthermore, as a mask for connection holes (contact holes), the one subjected to mask blank inspection through the apparatus and method according to the first to third embodiments is used, which is confirmed as having no defect in the mask blank state. Since the area of the connection holes is small and the pattern density is on the order of 5%, a ratio at which a defect occurs near any of the contact hole was small, and yields of mask blanks usable through the present method was high. The yields of the semiconductor devices manufactured according to the fourth embodiment were higher than those of the semiconductor devices manufactured with the conventional mask blank defect inspection.

In the foregoing, the invention made by the inventors of the present invention has been concretely described based on the embodiments. However, it is needless to say that the present invention is not limited to the foregoing embodiments and various modifications and alterations can be made within the scope of the present invention The present invention can be used in manufacturing industries for manufacturing mask blank inspection systems, mask blank, semiconductor devices, electronics, and others.

What is claimed is:

1. A method for mask blank defect inspection comprising:
   a first step including: radiation on a first mask blank having formed thereon a dot pattern serving as a reference with extreme ultraviolet light; and obtainment of a first focus position where a signal intensity of a first darkfield detection image produced by the scatter-reflected light is maximum;
   a second step including: radiation at the first focus position on a second mask blank, which is an inspection target with extreme ultraviolet light; scanning on the second mask blank in a direction perpendicular to an optical axis of the scatter-reflected light; and detection of a signal intensity of a second darkfield detection image produced by the scatter-reflected light;
   a third step including detection of a defect in the second mask blank based on the signal intensity of the second darkfield detection image;
   a fourth step including: radiation on a surface of a glass substrate, which is a base of the second mask blank with any one or all of visible light, ultraviolet light, and far-ultraviolet light; detection of a defect on the glass substrate by using reflected light; and extraction of a glass substrate which has a value of defects equal to or smaller than a specified value;
   a fifth step including: formation of the second mask blank by making a multilayer adhere to the glass substrate which has a value of defects equal to or smaller than the specified value
   a sixth step including: radiation on a fourth mask blank having formed thereon a line pattern serving as a reference with extreme ultraviolet light; and obtainment of a third focus position where a signal intensity of a fifth darkfield detection image produced by the scatter-reflected light is maximum;
   a seventh step including: radiation at the third focus position on the second mask blank, which is an inspection target with extreme ultraviolet light; scanning on the second mask blank in a direction perpendicular to an optical axis of the scatter-reflected light; and detection of a signal intensity of a sixth darkfield detection image produced by the scatter-reflected light;
   an eighth step including detection of a defect position in the second mask blank based on the signal intensity of the sixth darkfield detection image;
   a ninth step including: radiation on the second mask blank with extreme ultraviolet light while changing the focus position at the defect position; and detection of a signal intensity of a seventh darkfield detection image produced by the scatter-reflected light;

a tenth step of obtaining a fourth focus position where a signal intensity of the seventh darkfield detection image is maximum;

an eleventh step of determining a type of the defect in the second mask blank based on the third and fourth focus positions; and a twelfth step of outputting to a user a determination of the type of defect that is detected.

2. The method for mask blank defect inspection according to claim 1, wherein, in the eleventh step, the defect is determined as a dot-shaped defect when the fourth focus position is away from a signal light-receiving system compared to the third focus position, the defect is determined as a hole-shaped defect when the fourth focus position is closer thereto, and the defect is determined as a line-shaped defect when the fourth focus position is closer to the third focus position.

* * * * *

UNITED STATES PATENT AND TRADEMARK OFFICE
CERTIFICATE OF CORRECTION

| | | |
|---|---|---|
| PATENT NO. | : 7,630,068 B2 | Page 1 of 1 |
| APPLICATION NO. | : 11/707127 | |
| DATED | : December 8, 2009 | |
| INVENTOR(S) | : Tanaka et al. | |

It is certified that error appears in the above-identified patent and that said Letters Patent is hereby corrected as shown below:

On the Title, Item (73) Assignee please delete:

"Renesas Technology Corporation."

and insert:

--Renesas Technology Corp.--

Signed and Sealed this

Twenty-fifth Day of May, 2010

David J. Kappos
*Director of the United States Patent and Trademark Office*